(12) United States Patent
Ichihashi et al.

(10) Patent No.: US 9,192,781 B2
(45) Date of Patent: Nov. 24, 2015

(54) RADIOTHERAPY SYSTEM AND CONTROL METHOD FOR RADIOTHERAPY SYSTEM

(75) Inventors: Masahide Ichihashi, Otawara (JP); Masanori Koyama, Nasushiobara (JP)

(73) Assignees: KABUSHIKI KAISHA TOSHIBA, Tokyo (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 0 days.

(21) Appl. No.: 13/457,635

(22) Filed: Apr. 27, 2012

(65) Prior Publication Data

US 2012/0207372 A1  Aug. 16, 2012

Related U.S. Application Data

(63) Continuation of application No. PCT/JP2011/066143, filed on Jul. 14, 2011.

(30) Foreign Application Priority Data

Jul. 15, 2010 (JP) ................................. 2010-160988
Jul. 20, 2010 (JP) ................................. 2010-162847

(51) Int. Cl.
*G06K 9/00* (2006.01)
*A61N 5/10* (2006.01)
*A61B 6/00* (2006.01)

(52) U.S. Cl.
CPC ................. *A61N 5/103* (2013.01); *A61B 6/542* (2013.01); *A61B 6/488* (2013.01); *A61N 5/1048* (2013.01); *A61N 2005/1091* (2013.01)

(58) Field of Classification Search
USPC ....................................................... 382/132
See application file for complete search history.

(56) References Cited

U.S. PATENT DOCUMENTS 7,496,173 B2 * 2/2009 Goldman et al. ............... 378/65
2002/0021830 A1 * 2/2002 Ritt .............................. 382/132

(Continued)

FOREIGN PATENT DOCUMENTS

JP       10-146395      6/1998
JP       2002-126106 A  5/2002

(Continued)

OTHER PUBLICATIONS

International Preliminary Report on Patentability Issued Feb. 12, 2013 in PCT/JP2011/066143.

(Continued)

*Primary Examiner* — Hadi Akhavannik
(74) *Attorney, Agent, or Firm* — Oblon, McClelland, Maier & Neustadt, L.L.P.

(57) ABSTRACT

A radiotherapy system has: a placing unit placing a subject; an imaging unit performing an imaging of the subject; a region setting unit setting a required region of first image data obtained by the imaging unit performing the imaging of the subject and setting a corresponding required region of second image data obtained by, before the imaging, performing a pre-imaging of the subject; a histogram generating unit generating a dose-volume histogram of the required region of the first image data and generating a dose-volume histogram of the required region of the second image data; a difference computing unit computing a difference between the dose-volume histogram of the required region of the first image data and the dose-volume histogram of the required region of the second image data; and an outputting unit, if it is determined that the difference is greater than a threshold value, outputting the determination to an outside.

19 Claims, 18 Drawing Sheets

(56) References Cited

U.S. PATENT DOCUMENTS

| | | | |
|---|---|---|---|
| 2002/0080915 A1* | 6/2002 | Frohlich | 378/65 |
| 2003/0065260 A1* | 4/2003 | Cheng et al. | 600/427 |
| 2005/0077459 A1 | 4/2005 | Engler et al. | |
| 2006/0274924 A1* | 12/2006 | West et al. | 382/131 |
| 2006/0293583 A1 | 12/2006 | Saracen et al. | |
| 2008/0152085 A1 | 6/2008 | Saracen et al. | |
| 2008/0269568 A1* | 10/2008 | Lewis et al. | 600/300 |
| 2009/0003523 A1 | 1/2009 | Raanes et al. | |
| 2009/0129556 A1* | 5/2009 | Ahn | 378/208 |
| 2009/0262894 A1 | 10/2009 | Shukla et al. | |

FOREIGN PATENT DOCUMENTS

| | | |
|---|---|---|
| JP | 2003-522576 | 7/2003 |
| JP | 2004-510466 A | 4/2004 |
| JP | 2009-226015 A | 10/2009 |
| JP | 2010-69086 A | 4/2010 |
| WO | WO 01/60236 A2 | 8/2001 |
| WO | WO 02/13908 A2 | 2/2002 |
| WO | WO 2004/073655 A2 | 9/2004 |
| WO | WO 2008/000278 A1 | 1/2008 |

OTHER PUBLICATIONS

International Search Report mailed on Oct. 18, 2011, issued for Inernational Application No. PCT/JP2011/066143, filed on Jul. 14, 2011.

Extended European Search Report issued Nov. 13, 2013 in Patent Application No. 11806872.5.

Extended European Search Report dated Aug. 14, 2014, in European Patent Application No. 14171617.5.

Office Action issued Jul. 8, 2014, in Japanese Patent Application No. 2010-162847.

\* cited by examiner

DISPLAY IMAGE BASED ON
TREATMENT PLAN VOLUME DATA VP

DISPLAY IMAGE BASED ON
PRETREATMENT VOLUME DATA VQ

DISPLAY IMAGE OF CONTOUR SQ OF OAR
BASED ON PRETREATMENT VOLUME DATA VQ

DISPLAY IMAGE BASED ON
ALIGNED TREATMENT PLAN VOLUME DATA

RADIOTHERAPY SYSTEM AND CONTROL METHOD FOR RADIOTHERAPY SYSTEM

CROSS-REFERENCE TO RELATED APPLICATION

This application is based upon and claims the benefit of priority from Japanese Patent Application No. 2010-160988, filed on Jul. 15, 2010, and Japanese Patent Application No. 2010-162847, filed on Jul. 20, 2010, all of which are incorporated herein by reference.

FIELD

Embodiments according to the present invention relate to a radiotherapy system and a control method for the radiotherapy system that can carry out radiotherapy.

BACKGROUND

In radiotherapy, image data is generated by imaging during treatment planning, and treatment plan data is generated based on the image data. In addition, image data is generated by imaging just before the treatment. Then, the image data obtained just before the treatment is aligned with the image data for the treatment plan to compute a difference of the image data obtained just before the treatment from the image data for the treatment plan, and then repositioning is carried out by shifting the patient by the difference from the imaging position just before the treatment. After the repositioning, radiotherapy is carried out by irradiating a treatment site of the patient.

Examples of conventional arts relating to the embodiments include Japanese Patent Application Publication (Laid-Open: KOKAI) No. 2010-69086.

However, according to the conventional arts, because both images are aligned with each other based on shading (CT values, image density, values of luminance, or the like) of overall data of both the images including sites unrelated to treatment, shift of internal organs in the data of both the images tends not to be taken into account and an area of interest such as a treatment site may not be aligned with high accuracy. In particular, in the case where chest and abdominal organs such as a lung, a liver, and the like are irradiated, because of respiratory movement of an affected part, a normal site other than a treatment site might be irradiated.

BRIEF DESCRIPTION OF THE DRAWINGS

In accompanying drawings.

DETAILED DESCRIPTION

Radiotherapy systems and control methods for the radiotherapy systems of the embodiments will be described with reference to the accompanying drawings.

To solve the above-described problems, the present embodiments provide the radiotherapy system includes: a placing unit configured to place a subject; an imaging unit configured to perform an imaging of the subject; a region setting unit configured to set a required region of first image data obtained by the imaging unit performing the imaging of the subject and to set a corresponding required region of second image data obtained by, before the imaging, performing a pre-imaging of the subject; a histogram generating unit configured to generate a dose-volume histogram of the required region of the first image data and to generate a dose-volume histogram of the required region of the second image data; a difference computing unit configured to compute a difference between the dose-volume histogram of the required region of the first image data and the dose-volume histogram of the required region of the second image data; and an outputting unit configured to, if it is determined that the difference is greater than a threshold value, output the determination to an outside.

To solve the above-described problems, the present embodiments provide the radiotherapy system includes: a placing unit configured to place a subject; an imaging unit configured to perform an imaging of the subject; an image storage unit configured to store therein first image data obtained by performing a pre-imaging of the subject in radiotherapy planning; a region storage unit configured to store therein position information of a required region included in the first image data; and an image aligning unit configured to use the position information of the required region to align the first image data with second image data obtained by the imaging unit performing the imaging of the subject before radiotherapy.

To solve the above-described problems, the present embodiments provide the control method for the radiotherapy system includes: performing an imaging of a subject; setting a required region of first image data obtained by the imaging unit performing the imaging of the subject and setting a corresponding required region of second image data obtained by, before the imaging, performing a pre-imaging of the subject; generating a dose-volume histogram of the required region of the first image data and generating a dose-volume histogram of the required region of the second image data; computing a difference between the dose-volume histogram of the required region of the first image data and the dose-volume histogram of the required region of the second image data; and outputting the determination to an outside if it is determined that the difference is greater than a threshold value.

First Embodiment

Figure 1:
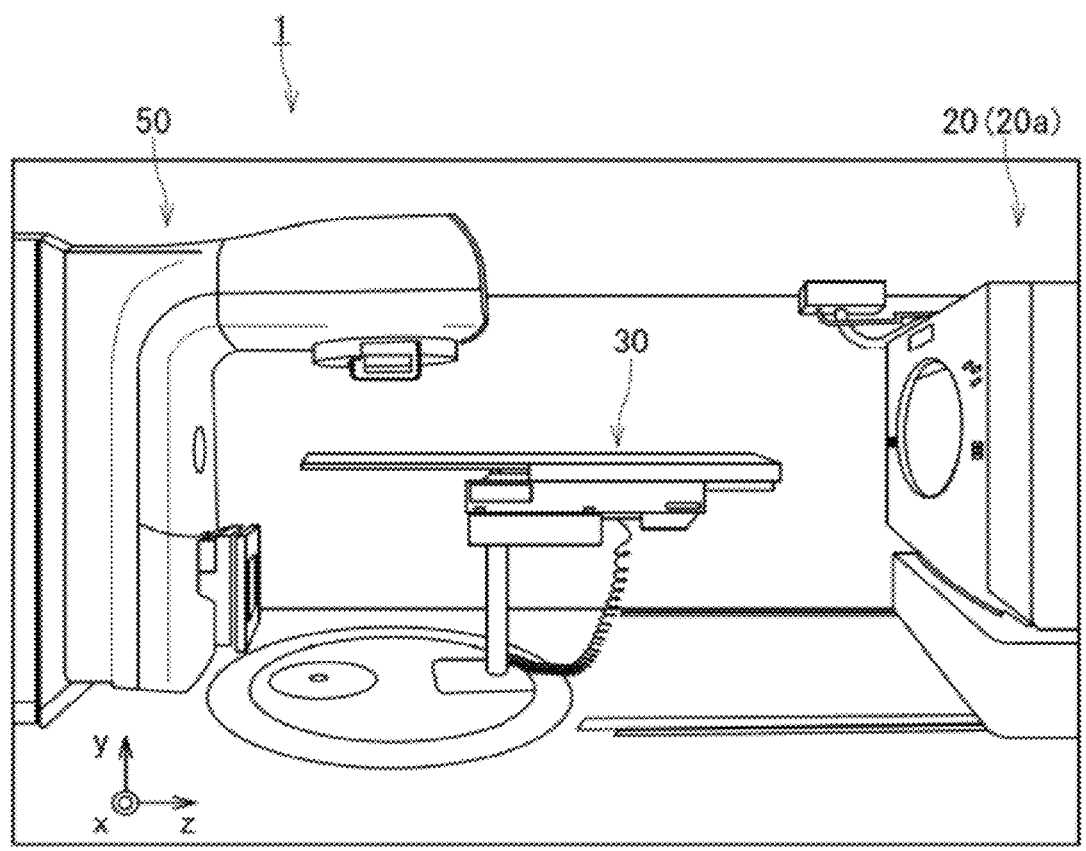
FIG. 1 is an external view diagram showing a part of a radiotherapy system of a first embodiment.
Figure 2:
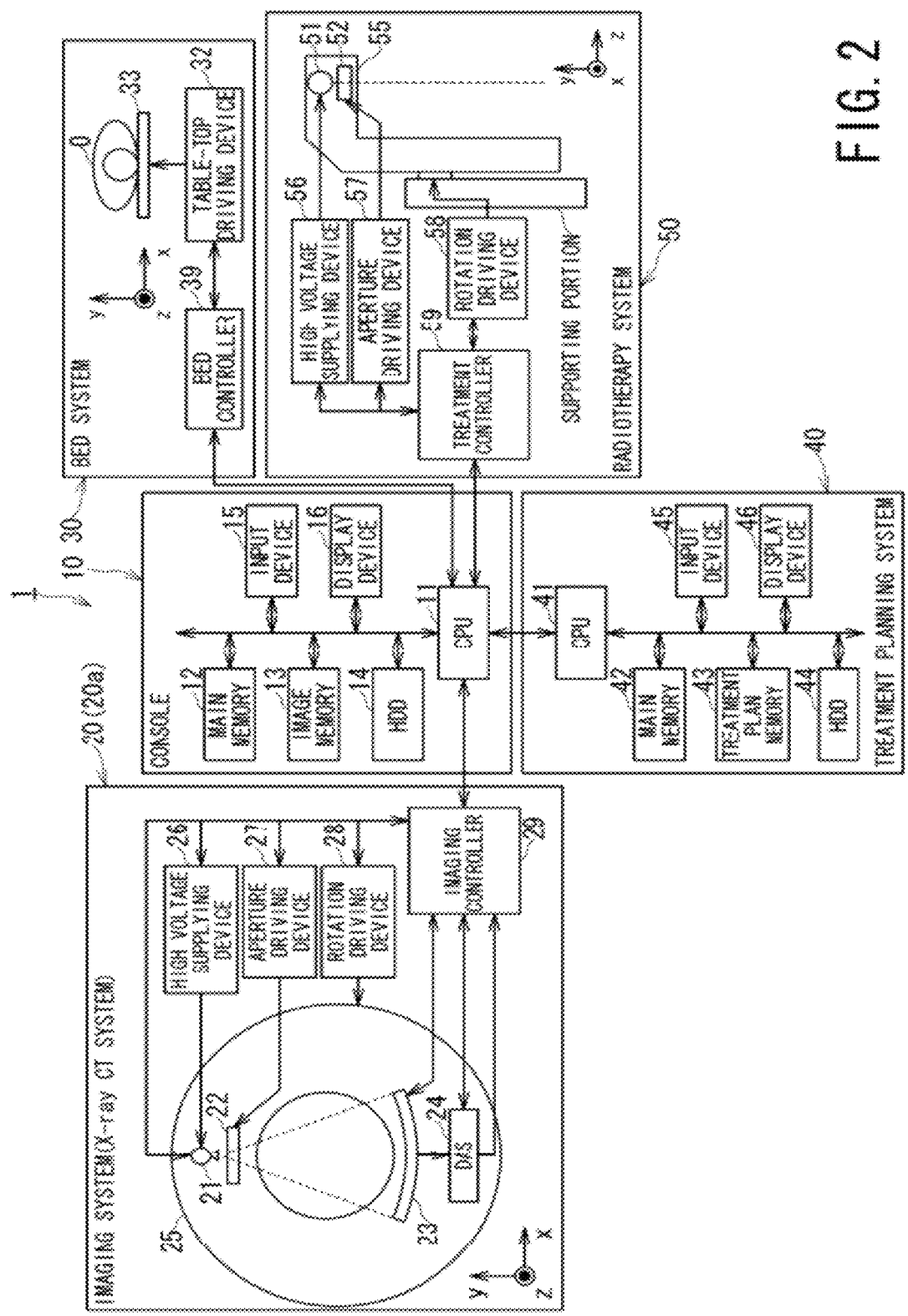
FIG. 2 is a block diagram showing an entirety of the radiotherapy system of the first embodiment.

FIG. 1 is an external view showing a part of a radiotherapy system of a first embodiment. FIG. 2 is a block diagram showing the entirety of the radiotherapy system of the first embodiment.

FIGS. 1 and 2 show the radiotherapy system 1 of the first embodiment. The radiotherapy system 1 includes a console 10, an imaging system 20, a bed system 30, a treatment planning system 40, and a radiotherapy system (linac: a radiotherapy system that carries out treatment by irradiation based on treatment plan data) 50.

As shown in FIG. 1, the imaging system 20, the bed system 30, and the radiotherapy system 50 are usually installed in an examination room. On the other hand, the console 10 is usually installed in a control room adjacent to the examination room. The treatment planning system 40 is installed outside the examination room and the control room. However, the treatment planning system 40 may be installed in the control room or may be an integrated apparatus with the console 10. Also, representative examples of the imaging system 20 include an X-ray CT system, an MRI (magnetic resonance imaging) apparatus, and an X-ray apparatus. The following describes the case in which an X-ray CT system 20a is used as the imaging system 20.

As shown in FIG. 2, the console 10 of the radiotherapy system 1 has a computer-based configuration and is able to communicate with a trunk network of a hospital such as a LAN (local area network), not shown. The console 10 is broadly composed of basic hardware such as a CPU (central processing unit) 11, main memory 12, image memory 13, an HDD (hard disc drive) 14, an input device 15, and a display device 16. The CPU 11 and each hardware component of the console 10 are connected with each other via buses as common signal transmission paths. In addition, the console 10 may include a recording medium drive.

The CPU 11 is a control device having a configuration of an integrated circuit (LSI) in which an electronic circuit composed of a semiconductor is housed in a package with multiple terminals. If an instruction is input by an operator such as a physician operating the input device 15, the CPU 11 executes a program stored in the main memory 12. Alternatively, the CPU 11 loads a program stored in the HDD 14, a program transferred from the network and installed in the HDD 14, or a program read out from a recording medium mounted in a recording medium drive (not shown) and installed in the HDD 14, into the main memory 12 to execute the program.

The main memory 12 is a storage device that includes ROM (read only memory), RAM (random access memory), or the like. The main memory 12 is used for storage of IPL (initial program loading), a BIOS (basic input/output system), and data. Also, the main memory 12 is used as working memory for the CPU 11 and to temporarily store data.

The image memory 13 is a storage device in which slice data as two-dimensional image data and treatment plan volume data and pretreatment volume data as three-dimensional image data are stored.

The HDD 14 is a storage device containing undetachable metal disks on which a magnetic substance is applied or evaporated. The HDD 14 is a storage device in which programs installed in the console 10 (in addition to application programs, including an OS (operating system)) and data are stored. In addition, the OS may be allowed to provide a GUI (graphical user interface) that makes heavy use of graphics in information displayed on the display device 16 so that an operator such as an operational person can perform basic operations through the input device 15.

The input device 15 is a pointing device that can be operated by the operator and input signals according to operations are sent to the CPU 11.

The display device 16 includes an image combining circuit, VRAM (video random access memory), and a display that are not shown. The image combining circuit generates composite data into which character data of a variety of parameters is combined with image data. The VRAM expands the composite data into display image data to be displayed on the display. The display is composed of a liquid crystal display, a CRT (cathode ray tube), or the like, and sequentially displays items of the display image data as display images.

The console 10 controls operations of an X-ray CT system 20a, a bed system 30, and a radiotherapy system 50. The console 10 also performs correction processing (preprocessing) such as logarithmic transformation processing and sensitivity correction on raw data input from a DAS 24 of the X-ray CT system 20a to generate projection data, and generates slice data as two-dimensional image data and volume data as three-dimensional image data on the basis of the projection data.

To display image data of a region including a treatment site of a cancer, a tumor, or the like of a patient (subject) 0, the X-ray CT system 20a of the radiotherapy system 1 images the region including the treatment site. The X-ray CT system 20a includes an X-ray tube 21 as a radiation source, an aperture 22, an X-ray detector 23, the DAS (data acquisition system) 24, a rotation portion 25, a high voltage supplying device 26, an aperture driving device 27, a rotation driving device 28, and an imaging controller 29.

The X-ray tube 21 causes an electron beam to collide with a metal target according to tube voltage supplied from the high voltage supplying device 26 to generate bremsstrahlung X-rays, and applies the X-rays to the X-ray detector 23. The X-rays applied from the X-ray tube 21 form fan beam X-rays and cone beam X-rays.

Using the aperture driving device 27, the aperture 22 adjusts an area being irradiated with the X-rays by the X-ray tube 21. That is, the X-ray irradiated area can be modified by the aperture driving device 27 adjusting an opening of the aperture 22.

The X-ray detector 23 is a matrix form X-ray detector, that is, the X-ray detector 23 is a two-dimensional array type X-ray detector (also referred to as a multi-slice type sensor) having a plurality of channels in a channel direction and a plurality of rows of X-ray detecting elements in a slice direction. The X-ray detecting elements of the X-ray detector 23 detect the X-rays applied from the X-ray tube 21.

The DAS 24 amplifies a signal of transmission data detected by each X-ray detecting element of the X-ray detector 23 to convert the signal into a digital signal. Output data of the DAS 24 is supplied to the console 10 through the imaging controller 29.

The rotation portion 25 holds the X-ray tube 21, the aperture 22, the X-ray detector 23, and the DAS 24 as a single unit. The rotation portion 25 can rotate about the patient O with the X-ray tube 21, the aperture 22, the X-ray detector 23, and the DAS 24 as a single unit and with the X-ray tube 21 and the X-ray detector 23 opposing each other. It is assumed that a direction parallel to an axis of rotation of the rotation portion 25 is defined as a z axis direction, and a plane orthogonal to the z axis direction is defined as an x axis direction and a y axis direction.

The high voltage supplying device 26 supplies the X-ray tube 21 with power required for X-ray irradiation in response to control of the imaging controller 29.

The aperture driving device 27 has a mechanism that uses the aperture 22 to adjust an area irradiated with X-rays in the slice direction in response to control of the imaging controller 29.

The rotation driving device 28 has a mechanism that, in response to control of the imaging controller 29, rotates the rotation portion 25 about a cavity portion (not shown) with a position relationship of the rotation portion 25 maintained.

The imaging controller 29 comprises a CPU and a memory. The imaging controller 29 controls the X-ray tube 21, the X-ray detector 23, the DAS 24, the high voltage supplying device 26, the aperture driving device 27, and the rotation driving device 28 to perform a scan with the operations of the bed system 30.

The bed system 30 of the radiotherapy system 1 includes a table-top driving device 32, a table-top 33, and a bed controller 39.

The patient O can be placed on the table-top 33. The table-top driving device 32 has a mechanism that moves the table-top 33 up and down along the y axis direction and moves the table-top 33 backward and forward along the z axis direction in response to control of the bed controller 39. The table-top driving device 32 also has a mechanism that rotates the table-top 33 about the y axis direction in response to control of the bed controller 39.

The bed controller 39 comprises a CPU and a memory. The bed controller 39 controls the table-top driving device 32 to perform a scan with the operations of the X-ray CT system 20a. The bed controller 39 also controls the table-top driving device 32 to perform radiotherapy with the operations of the radiotherapy system 50.

The treatment planning system 40 of the radiotherapy system 1 generates treatment plan data for radiotherapy to be carried out by the radiotherapy system 50 on the basis of the slice data and the volume data generated by the console 10 after imaged by the X-ray CT system 20a. Under the control of the console 10 based on the treatment plan data generated by the treatment planning system 40, a site to be treated of the patient O is irradiated by the radiotherapy system 50. The treatment planning system 40 has a computer-based configuration and can communicate with the trunk network of the hospital such as a LAN, not shown. The treatment planning system 40 is broadly composed of basic hardware such as a CPU 41, main memory 42, treatment plan memory 43, an HDD 44, an input device 45, and a display device 46. The CPU 41 and each hardware component of the treatment planning system 40 are connected with each other via buses as common signal transmission paths. In addition, the treatment planning system 40 may include a recording medium drive.

A configuration of the CPU 41 is equivalent to that of the CPU 11 of the console 10. If the operator operates the input device 45 to input an instruction, the CPU 41 executes a program stored in the main memory 42. Alternatively, the CPU 41 loads a program stored in the HDD 44, a program transferred from the network and installed in the HDD 44, or a program read out from a recording medium mounted in a recording medium drive (not shown) and installed in the HDD 44, into the main memory 42 to execute the program.

A configuration of the main memory 42 is equivalent to that of the main memory 12 of the console 10. The main memory 42 is used for storage of IPL, a BIOS, and data. Also, the main memory 42 is used as working memory for the CPU 41 and to temporarily store data.

The treatment plan memory 43 is a storage device in which treatment plan data is stored.

A configuration of the HDD 44 is equivalent to that of the HDD 14 of the console 10.

A configuration of the input device 45 is equivalent to that of the input device 15 of the console 10.

A configuration of the display device 46 is equivalent to that of the display device 16 of the console 10.

The treatment planning system 40 determines a position of the treatment site of the patient O and a shape of the treatment site based on the image data generated by the X-ray CT system 20a, and also determines a type of radiation (an X-ray, an electron beam, a neutron beam, a proton beam, a heavy particle beam, or the like) to be applied to the treatment site, energy of the radiation, and a radiation field.

The radiotherapy system 50 of the radiotherapy system 1 can generally generate radiation in the MV range. The radiotherapy system 50 is provided with the aperture (collimator) at a radiation generation port, and the aperture provides an irradiation shape and a dose distribution that are based on the treatment plan. In recent years, multileaf collimators (MLCs) that can form dose distributions corresponding to complex shapes of tumors by a plurality of movable leaves have been often used as the apertures. The radiotherapy system 50 adjusts an irradiation amount with a radiation field formed by the aperture and eliminates or reduces a treatment site of the patient O. A combination of the X-ray CT system 20a, the bed system 30, and the radiotherapy system 50 is called a "linac-CT."

The radiotherapy system 50 includes a radiation source 51 as a radiation source, an aperture 52, an arm portion 55, a high voltage supplying device 56, an aperture driving device 57, a rotation driving device 58, and a treatment controller 59.

The radiation source 51 generates radiation according to tube voltage supplied from the high voltage supplying device 56.

Using the aperture driving device 57, the aperture 52 adjusts an area being irradiated by the radiation source 51. That is, the irradiated area can be modified by the aperture driving device 57 adjusting an opening of the aperture 52.

The arm portion 55 holds the radiation source 51 and the aperture 52 as a single unit. The arm portion 55 can rotate about the patient O with the radiation source 51 and the aperture 52 as a single unit.

The high voltage supplying device 56 supplies the radiation source 51 with power required for irradiation in response to control of the treatment controller 59.

The aperture driving device 57 has a mechanism that uses the aperture 52 to adjust an irradiated area in response to control of the treatment controller 59.

The rotation driving device 58 has a mechanism that rotates the arm portion 55 about a connection portion (not shown) between the arm portion 55 and a supporting portion (not shown) in response to control of the treatment controller 59.

The treatment controller 59 comprises a CPU and a memory. The treatment controller 59 controls, in accordance with the treatment plan data generated by the treatment planning system 40, the radiation source 51, the high voltage supplying device 56, and the aperture driving device 57 to perform irradiation for treatment with the operations of the bed system 30.

Figure 3:
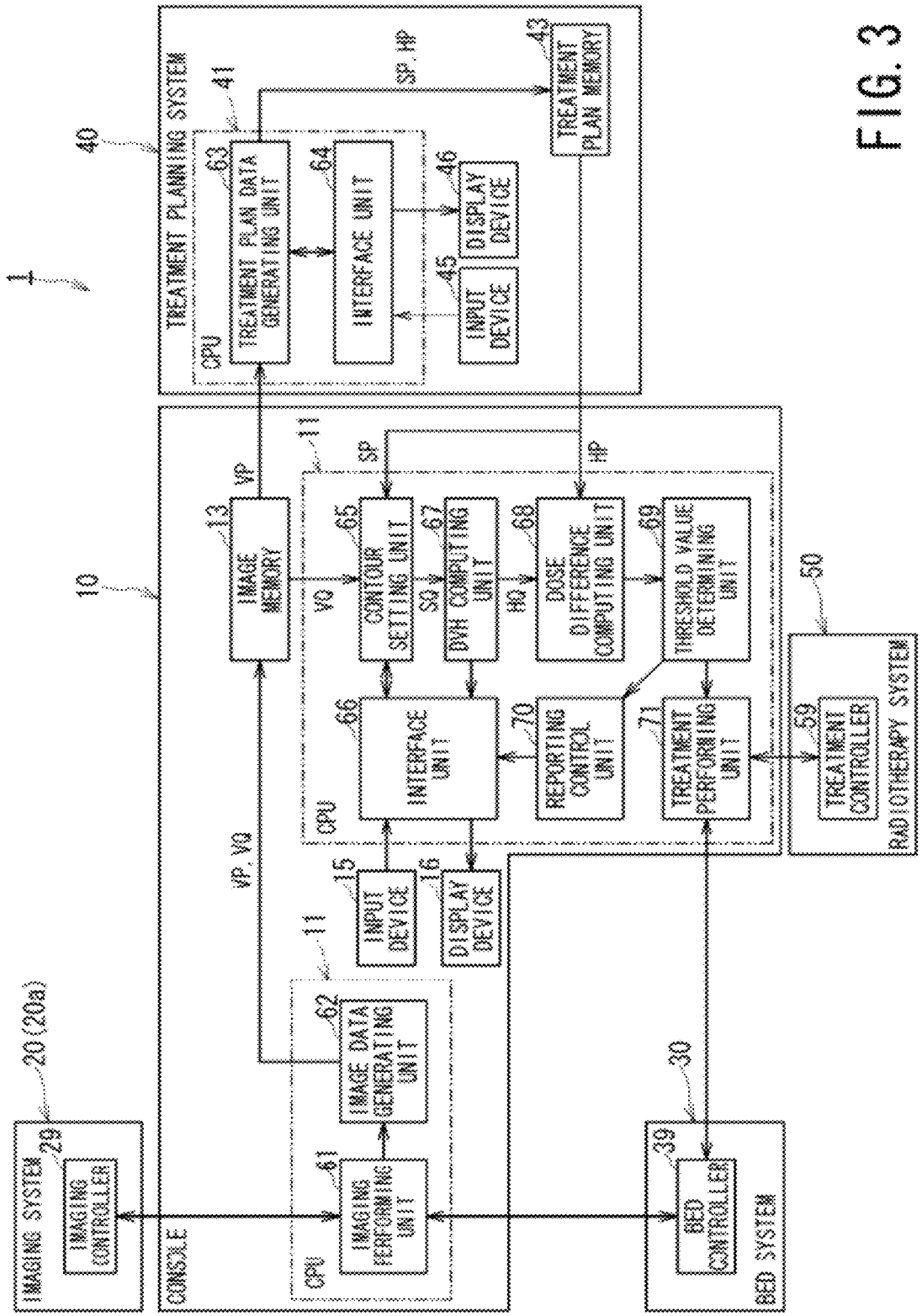
FIG. 3 is a block diagram showing functions of the radiotherapy system of the first embodiment.

FIG. 3 is a block diagram showing functions of the radiotherapy system 1 of the first embodiment.

The CPU 11 of the console 10 and the CPU 41 of the treatment planning system 40 execute programs, and thereby as shown in FIG. 3, the radiotherapy system 1 functions as an imaging performing unit 61, an image data generating unit 62, a treatment plan data generating unit 63, an interface unit 64, a contour setting unit 65, an interface unit 66, a DVH (dose-volume histogram) computing unit 67, a dose difference computing unit 68, a threshold value determining unit 69, a reporting control unit 70, and a treatment performing unit 71. All or a part of the components 61 to 71 of the radiotherapy system 1 may be included in the radiotherapy system 1 as hardware.

The imaging performing unit 61 of the console 10 has a function of controlling the operations of the imaging controller 29 of the X-ray CT system 20a and the bed controller 39 of the bed system 30 to, for a treatment plan, image a region including a treatment site of the patient O. Also, the imaging performing unit 61 has a function of controlling the operations of the imaging controller 29 of the X-ray CT system 20a and the bed controller 39 of the bed system 30 to image the region including the treatment site of the patient O after the treatment planning, for example, just before the treatment.

The image data generating unit 62 of the console 10 has a function of generating slice data as two-dimensional image data by the imaging performing unit 61 performing processing such as image reconstructing processing on the transmission data obtained by the X-ray CT system 20a. Also, the image data generating unit 62 has a function of generating volume data as three-dimensional image data based on the slice data corresponding to a plurality of slices. Specifically, the image data generating unit 62 generates the slice data by imaging it for a treatment plan and generates the volume data (treatment plan volume data) VP for the treatment plan for the treatment planning system 40. On the other hand, the image data generating unit 62 generates slice data by imaging it just before the treatment by the radiotherapy system 50 and generates volume data (pretreatment volume data) VQ obtained just before the treatment. Each of the volume data VP and the volume data VQ generated by the image data generating unit 62 is stored in a storage device such as the image memory 13.

Figure 4:
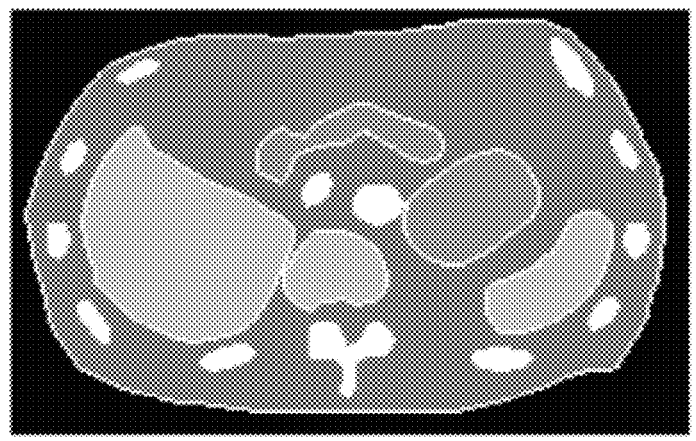
FIG. 4 is a diagram schematically showing an example of a display image based on a treatment plan volume data.
Figure 5:
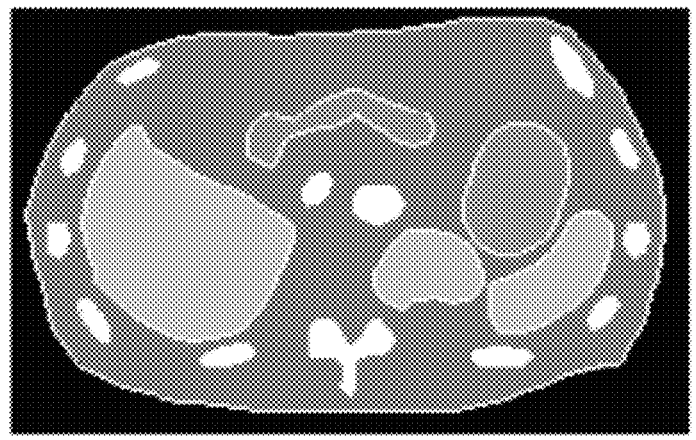
FIG. 5 is a diagram schematically showing an example of a display image based on a pretreatment volume data.

FIG. 4 is a diagram schematically showing an example of a display image based on the treatment plan volume data VP. FIG. 5 is a diagram schematically showing an example of a display image based on the pretreatment volume data VQ.

FIG. 4 shows a display image based on the treatment plan volume data VP. FIG. 5 shows a display image based on the pretreatment volume data VQ. If the display image shown in FIG. 4 is compared with the display image shown in FIG. 5, it can be seen that there is a difference between the volume data VP and the volume data VQ in structure images corresponding to the structure of the patient O.

Figure 6:
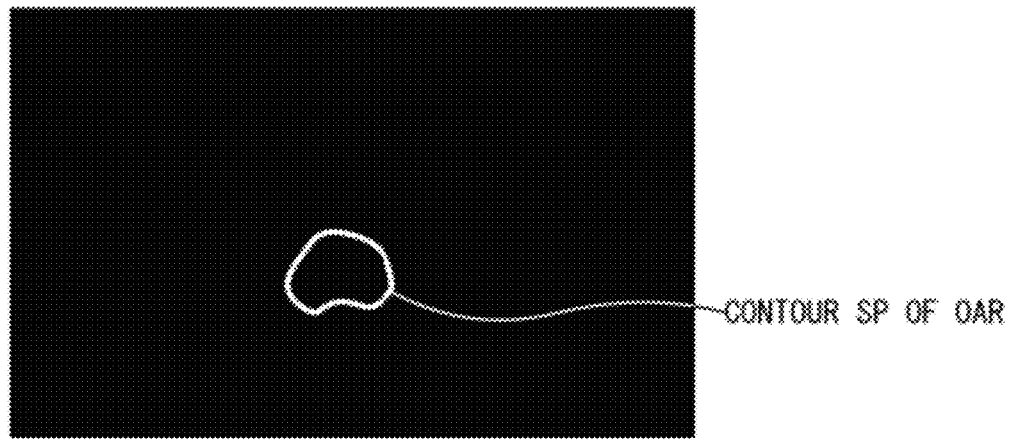
FIG. 6 is a diagram schematically showing an example of a display image of a contour of an OAR based on the treatment plan volume data.

The treatment plan data generating unit 63 of the treatment planning system 40 shown in FIG. 3 has a function of setting a treatment plan by setting irradiation conditions such as a direction and number of irradiation, and a radiation intensity with a contour of a body of the patient O and a region of an affected part taken into consideration based on the treatment plan volume data VP stored in the image memory 13, to generate treatment plan data. When generating the treatment plan data, the treatment plan data generating unit 63 sets, on the basis of the treatment plan volume data VP, a required area, for example, a contour SP of an OAR (organ at risk) not to be irradiated. For example, the treatment plan data generating unit 63 sets the contour SP of the OAR through the interface unit 64. The contour SP of the OAR set by the treatment plan data generating unit 63 is three-dimensional position information. When setting a contour SP of an OAR, the treatment plan data generating unit 63 may set a contour SP1 of only one OAR or may set contours SP1 SP2, . . . of a plurality of OARs. In addition, when generating the treatment plan data, the treatment plan data generating unit 63 may set a comparison point (isocenter). FIG. 6 is a diagram schematically showing an example of a display image of a contour SP of an OAR based on the treatment plan volume data VP.

Figure 7:
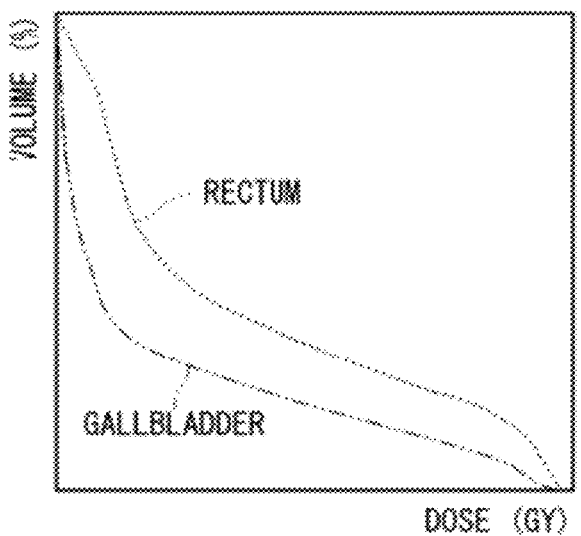
FIG. 7 is a diagram showing general DV histograms of OARs as required regions.
Figure 8:
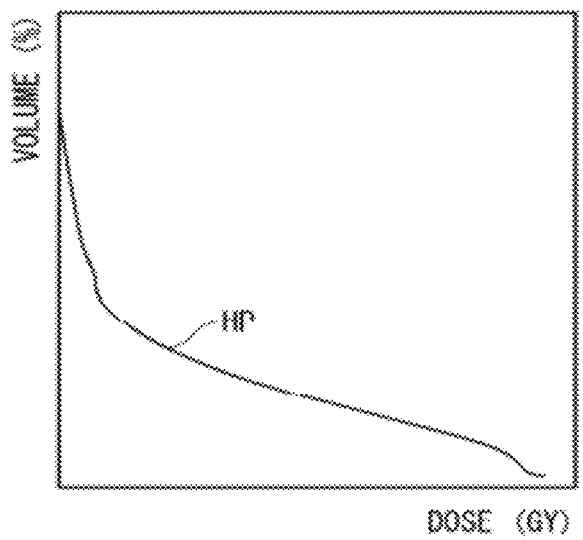
FIG. 8 is a diagram showing an example of a DV histogram of the contour of the OAR as the required region shown in FIG. 6.

In addition, when generating the treatment plan data, the treatment plan data generating unit 63 computes a DV histogram HP of the OAR based on the set contour SP of the OAR. The DV histogram computed by the treatment plan data generating unit 63 is a graph of relationship between dose and volume in a required region and is used for comparative evaluation of a plurality of items of treatment plan data. FIG. 7 is a diagram showing general DV histograms of OARs (a rectum and a gallbladder) as required regions. In addition, FIG. 8 is a diagram showing an example of a DV histogram HP of the contour SP of the OAR as the required region shown in FIG. 6.

It should be noted that it is assumed that the treatment plan data generating unit 63 generates the treatment plan data based on the treatment plan volume data VP generated by the X-ray CT system 20a included in the radiotherapy system 1, but the treatment plan data generating unit 63 is not limited thereto. The treatment plan data generating unit 63 may generate the treatment plan data based on treatment plan volume data generated by an imaging system external to the radiotherapy system 1. The treatment plan data generated by the treatment plan data generating unit 63 is stored in a storage device such as the treatment plan memory 43.

The interface unit 64 of the treatment planning system 40 is an interface such as a GUI that displays on the display device 46 a display image that is based on the treatment plan volume data VP and enables, on the display image, the operator to select the contour SP of the OAR through the input device 45 operated by the operator.

The contour setting unit 65 of the console 10 has a function of setting, on the basis of the pretreatment volume data VQ stored in the image memory 13, a contour SQ of the OAR corresponding to the contour SP of the OAR stored in the treatment plan memory 43. For example, the contour setting unit 65 sets the contour SQ of the OAR through the interface unit 66. Alternatively, the contour setting unit 65 aligns the volume data VP with the volume data VQ to set the contour SQ of the OAR corresponding to the contour SP of the OAR stored in the treatment plan memory 43. An aligning method may be a method for aligning the entire volume data VP with the entire volume data VQ so as to decrease a difference in CT values (image density, values of luminance, and the like) between the volume data VP and the volume data VQ, or may be a method for aligning the entire volume data VP with the entire volume data VQ using "non-rigid bodies" linked with modification and shift of the volume data VP and the volume data VQ.

Figure 9:
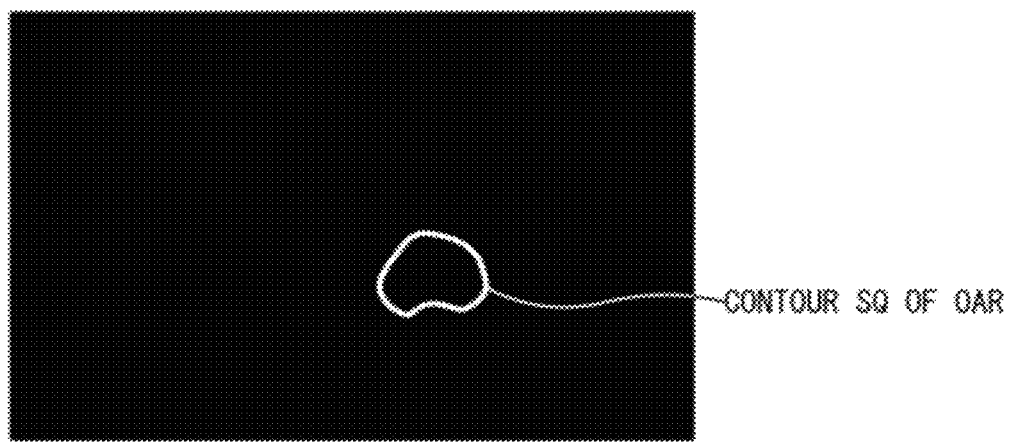
FIG. 9 is a drawing schematically showing an example of a display image of a contour of an OAR based on pretreatment volume data.

When setting the contour SQ of the OAR, the contour setting unit 65 sets only a contour SQ of one OAR (SQ1) if only a contour SP of one OAR (SP1) is set, and sets contours SQ of a plurality of OARs (SQ1, SQ2, . . . ) if contours SP of a plurality of OARs (SP1, SP2, . . . ) are set. FIG. 9 is a drawing schematically showing an example of a display image of a contour SQ of an OAR based on the pretreatment volume data VQ.

The interface unit 66 of the console 10 is an interface such as a GUI that displays on the display device 16 a display image that is based on the pretreatment volume data VQ stored in the image memory 13 and enables, on the display image, the operator to select the contour SQ through the input device 15 operated by the operator.

Figure 10:
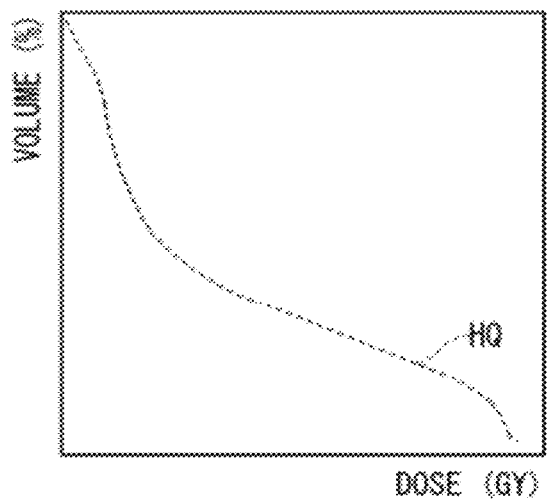
FIG. 10 is a diagram showing an example of a DV histogram of the contour of the OAR shown in FIG. 9.

The DVH computing unit 67 of the console 10 has a function of computing a DV histogram HQ of the OAR based on the contour SQ of the OAR set by the contour setting unit 65. The DV histogram HQ of the OAR computed by the DVH computing unit 67 is displayed on the display device 16 through the interface unit 66. FIG. 10 is a diagram showing an example of the DV histogram HQ of the contour SQ of the OAR shown in FIG. 9.

Figure 11:
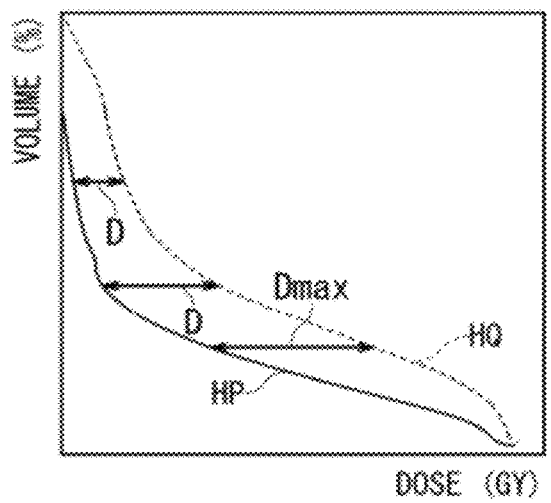
FIG. 11 is a diagram showing the DV histogram shown in FIG. 8, the DV histogram shown in FIG. 10, and the difference in each volume.

The dose difference computing unit 68 of the console 10 has a function of computing a difference D between doses in the same volume on the basis of the DV histogram HP stored in the treatment plan memory 43 and the DV histogram HQ computed by the DVH computing unit 67. That is, the dose difference computing unit 68 computes a difference D between the DV histograms HP and HQ in each volume. FIG. 11 is a diagram showing the DV histogram HP shown in FIG. 8, the DV histogram HQ shown in FIG. 10, and the difference D in each volume.

The threshold value determining unit 69 of the console 10 has a function of determining whether or not the difference D in each volume computed by the dose difference computing unit 68 is equal to or smaller than a threshold value. For example, the threshold value determining unit 69 determines whether or not a maximum difference Dmax (shown in FIG. 11) of the difference D in each of the volumes is equal to or smaller than a threshold value. If the maximum difference Dmax is greater than the threshold value, a position of the patient O seen when the treatment plan volume data VP is generated (during the imaging) is significantly different from a position of the patient O seen when the pretreatment volume data VQ is generated (during the imaging). Therefore, if the radiotherapy system 50 subsequently carries out irradiation, a position different from the position determined in the treatment planning is actually irradiated.

The reporting control unit 70 has a function of, if the threshold value determining unit 69 determines that the maximum difference Dmax is greater than the threshold value, reporting (output) an abnormality to the operator. For example, the reporting control unit 70 reports an abnormality to the operator through the display device 16.

The treatment performing unit 71 of the console 10 has a function of, if the threshold value determining unit 69 determines that a difference D is equal to or smaller than the threshold value, controlling the operations of the treatment controller 59 of the radiotherapy system 50 and the operations of the bed controller 39 of the bed system 30 to treat a treatment site of the patient O.

Figure 12:
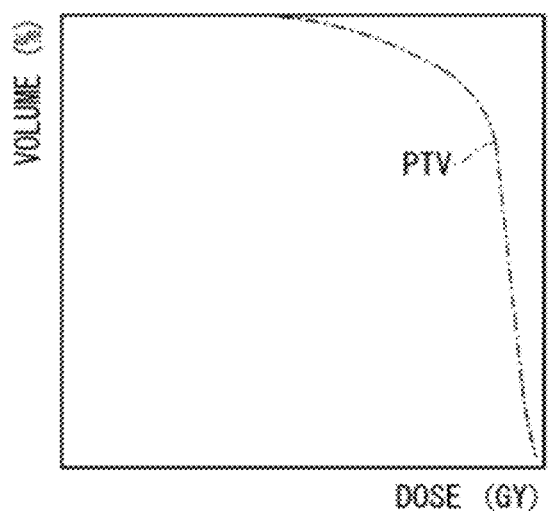
FIG. 12 is a diagram showing a general DV histogram of a PTV as a required region.

It should be noted that the contour SP of the required region set by the treatment plan data generating unit 63 and the contour setting unit 65 is not limited to a contour SP of an OAR. The contour SP of the required region set by the treatment plan data generating unit 63 and the contour setting unit 65 may be a contour SP of a PTV (planning target volume) as a treatment site. FIG. 12 is a diagram showing a general DV histogram of a PTV as a required region.

Next, a first operation of the radiotherapy system 1 of the first embodiment will be described using flow charts shown in FIG. 13 and FIG. 14.

If the patient O is placed on the table-top 33 of the bed system 30 of the radiotherapy system 1, the radiotherapy system 1 controls the operations of the bed controller 39 of the bed system 30 to insert the table-top 33 into an opening of the X-ray CT system 20a. Then, as shown in FIG. 13, the radiotherapy system 1 controls the operations of the imaging controller 29 of the X-ray CT system 20a to image a region including the treatment site of the patient O for treatment planning (step ST1). Then, the radiotherapy system 1 performs processing such as image reconstructing processing on transmission data obtained by the X-ray CT system 20a in step ST1 to generate slice data as two-dimensional image data, and generates treatment plan volume data VP as three-dimensional image data based on the slice data corresponding to a plurality of slices (step ST2). The treatment plan volume data VP generated in step ST2 is stored in a storage device such as the image memory 13 (step ST3).

The radiotherapy system 1 sets a treatment plan by setting irradiation conditions such as a direction and number of irradiation, and a radiation intensity with a contour of a body of the patient O and a region of an affected part taken into consideration based on the treatment plan volume data VP stored in the image memory 13 in step ST3, to generate treatment plan data (step ST4). In step ST4, the radiotherapy system 1 sets a contour SP of an OAR as a required region based on the treatment plan volume data VP (step ST4a). In step ST4, the radiotherapy system 1 also computes a DV histogram HP of the contour SP of the OAR set in step ST4a (step ST4b). The treatment plan data generated in step ST4 is stored in a storage device such as the treatment plan memory 43 (step ST5).

When the imaging of the region including the treatment site of the patient O ends in step ST1, the radiotherapy system 1 controls the operations of the bed controller 39 of the bed system 30 to retreat the table-top 33 from the opening of the X-ray CT system 20a. Then, the patient O is removed from the table-top 33 of the bed system 30 of the radiotherapy system 1.

If the patient O is placed on the table-top 33 of the bed system 30 of the radiotherapy system 1 just before the treatment is performed by the radiotherapy system 50, the radiotherapy system 1 controls the operations of the bed controller 39 of the bed system 30 to insert the table-top 33 into the opening of the X-ray CT system 20a. Then, as shown in FIG. 14, the radiotherapy system 1 controls the operations of the imaging controller 29 of the X-ray CT system 20a to image the region including the treatment site of the patient O just before the treatment (step ST11). Then, the radiotherapy system 1 performs processing such as image reconstructing processing on transmission data obtained by the X-ray CT system 20a in step ST11 to generate slice data as two-dimensional image data, and generates pretreatment volume data VQ as three-dimensional image data based on the slice data corresponding to a plurality of slices (step ST12). The pretreatment volume data VQ generated in step ST12 is stored in a storage device such as the image memory 13 (step ST13).

The radiotherapy system 1 sets a contour SQ of the OAR corresponding to the contour SP of the OAR stored in the treatment plan memory 43 based on the pretreatment volume data VQ stored in the image memory 13 in step ST13 (step ST14). The radiotherapy system 1 also computes a DV histogram HQ of the contour SQ of the OAR based on the treatment plan set in step ST4 and the contour SQ of the OAR set in step ST14 (step ST15).

Figure 13:
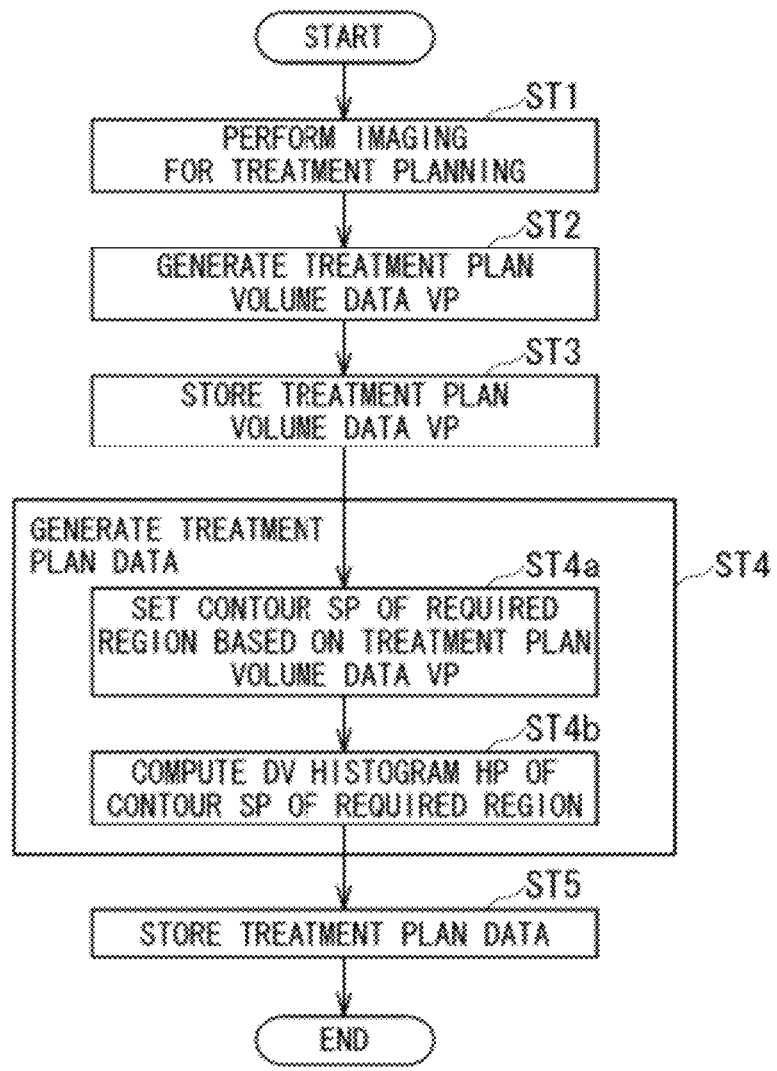
FIG. 13 is a flowchart showing a first operation of the radiotherapy system of the first embodiment.
Figure 14:
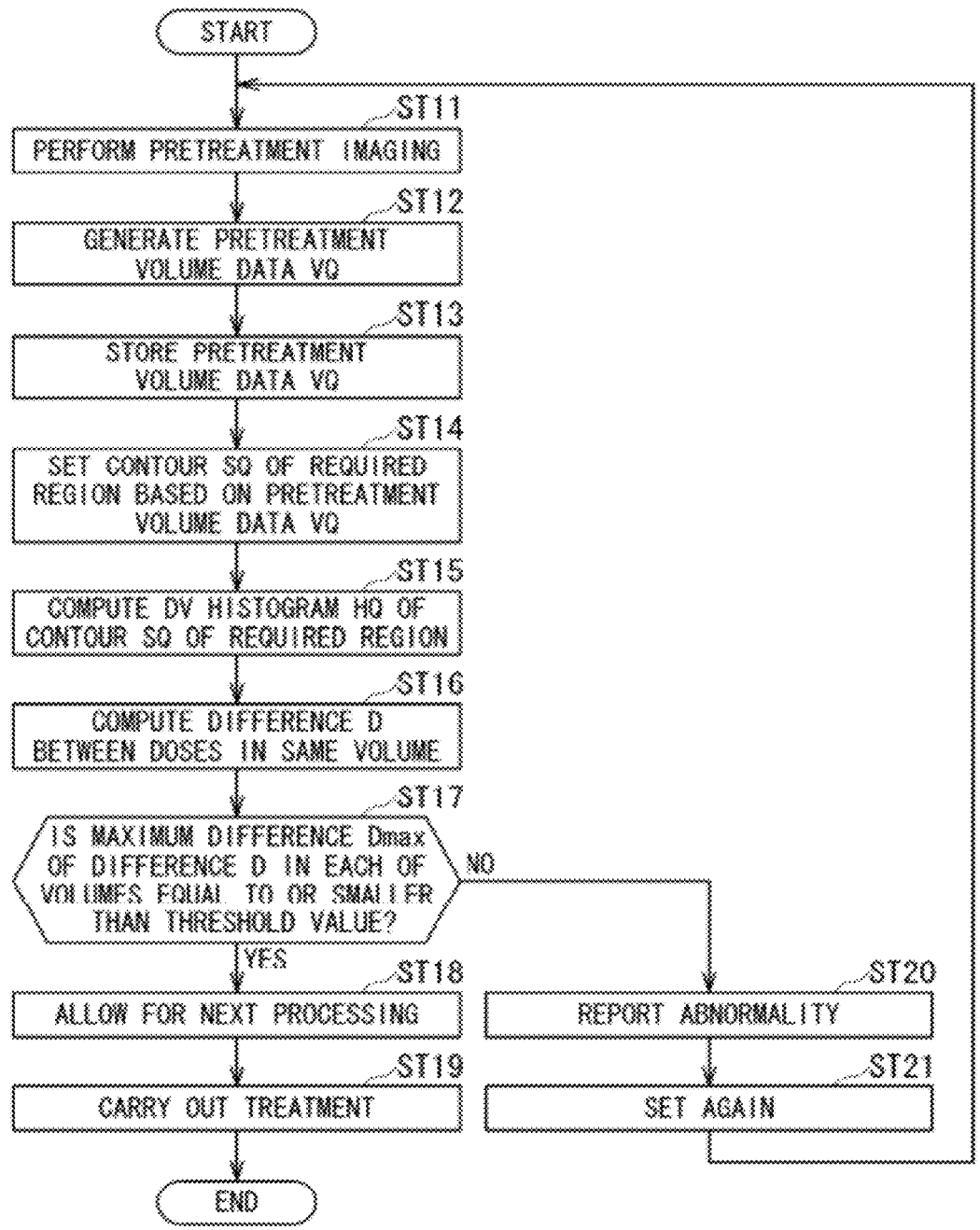
FIG. 14 is a flowchart showing the first operation of the radiotherapy system of the first embodiment.

Then, the radiotherapy system 1 computes differences D between doses in the same volumes based on the DV histogram HP of the contour SP of the OAR set in step ST4b in FIG. 13 and the DV histogram HQ of the contour SQ of the OAR set in step ST15 (step ST16).

Then, the radiotherapy system 1 determines whether or not a maximum difference Dmax of the difference D in each of the volumes computed in step ST16 is equal to or smaller than a threshold value (step ST17). If yes in step ST17, that is, if it is determined that the maximum difference Dmax of the difference D in each of the volumes is equal to or smaller than the threshold value, the radiotherapy system 1 allows for processing in a next step, the step ST19 (step ST18).

Then, the radiotherapy system 1 controls the operations of the treatment controller 59 of the radiotherapy system 50 to treat the treatment site of the patient O (step ST19). After the treatment site of the patient O is treated in step ST19, the radiotherapy system 1 controls the operations of the bed controller 39 of the bed system 30 to retreat the table-top 33 from the radiotherapy system 50. Then, the patient O is removed from the table-top 33 of the bed system 30 of the radiotherapy system 1.

On the other hand, if no in step ST17, that is, if it is determined that the maximum difference Dmax of the difference D in each of the volumes is greater than the threshold value, the radiotherapy system 1 reports an abnormality to the operator (step ST20). For example, in step ST20, the radiotherapy system 1 reports an abnormality to the operator through the display device 16. Then, after a setting is carried out again by shifting the patient O on the table-top (step ST21), the radiotherapy system 1 performs the pretreatment imaging (step ST11).

Figure 15:
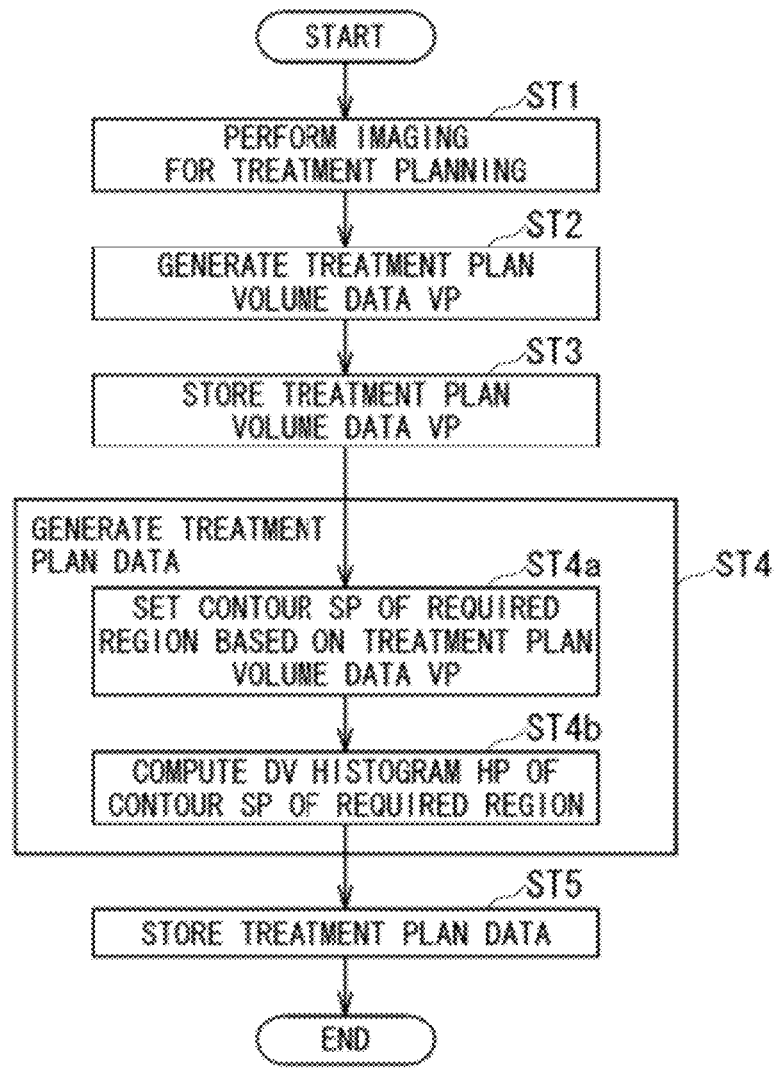
FIG. 15 is a flowchart showing a second operation of the radiotherapy system of the first embodiment.
Figure 16:
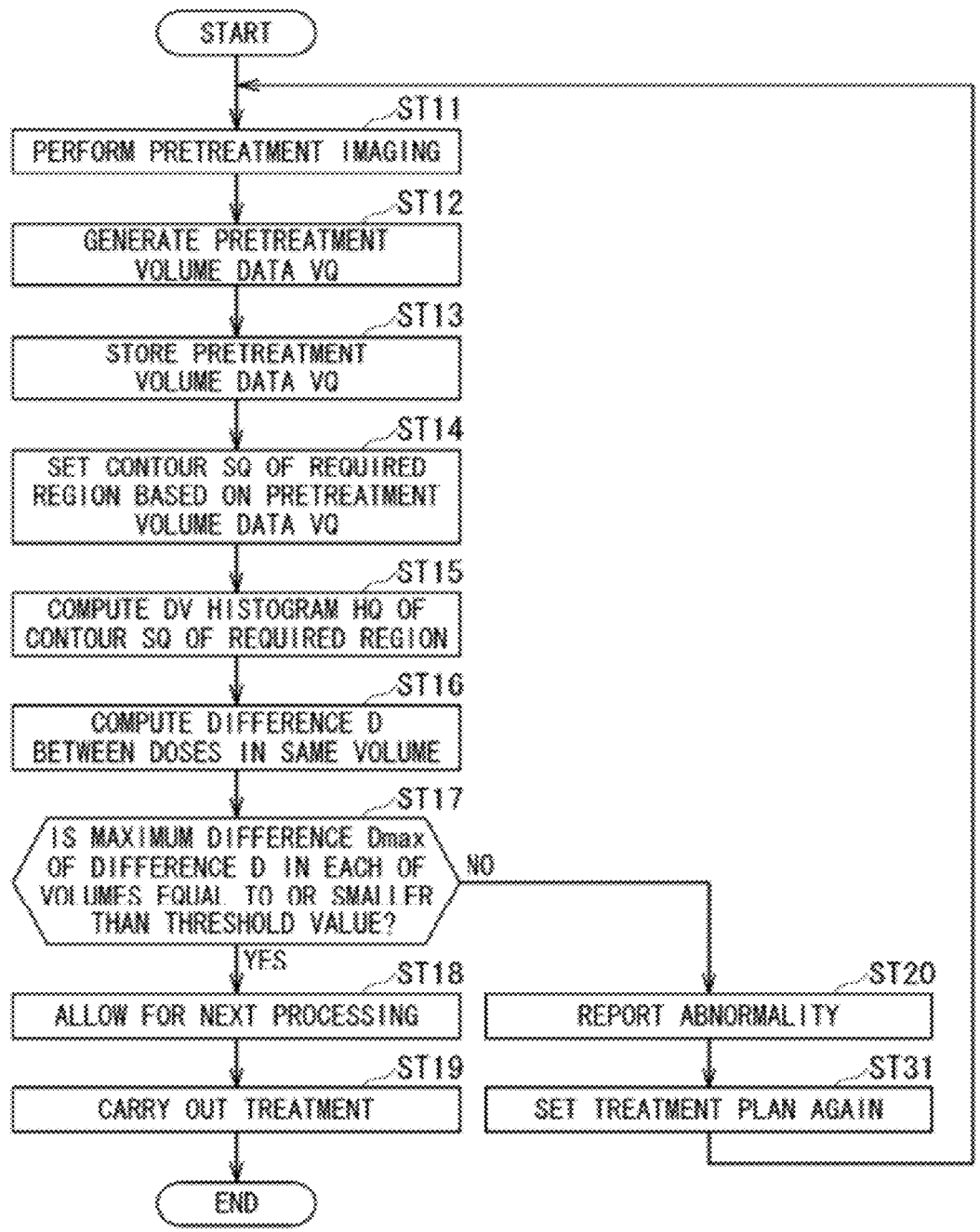
FIG. 16 is a flowchart showing the second operation of the radiotherapy system of the first embodiment.

Next, a second operation of the radiotherapy system 1 of the first embodiment will be described using flow charts shown in FIG. 15 and FIG. 16. In the second operation of the radiotherapy system 1 shown in FIG. 15 and FIG. 16, the same reference numerals are used for denoting the same steps as those in the first operation of the radiotherapy system 1 shown in FIG. 13 and FIG. 14 and descriptions thereof are omitted.

If the radiotherapy system 1 reports the abnormality to the operator in step ST20, the treatment planning system 40 reconsiders the treatment plan set in step ST4 and sets a treatment plan again (step ST31). For example, in step ST31, with the treatment plan set in step ST4 as an initial setting, the irradiation conditions such as a direction and number of irradiation, and radiation intensity are set again. Then, the radiotherapy system 1 computes a DV histogram HQ of the contour SQ of the OAR based on the treatment plan set again in step ST31 and the contour SQ of the OAR set in step ST14 (step ST15), and the processing proceeds to a step ST16.

In addition, the radiotherapy system 1 may also compute the DV histogram HQ of the contour SQ of the OAR associated with the irradiation conditions simultaneously as the irradiation conditions are set again in step ST31 to immediately display the DV histogram HQ. In this case, it is suitable to display the DV histogram HP computed in step ST4b with the DV histogram HQ, which is immediately displayed. The operator can judge suitability by comparing the immediately displayed DV histogram HQ with the DV histogram HP to allow for the processing in step ST19 without stopping by the step ST17.

According to the radiotherapy system 1 of the first embodiment, the DV histogram HP of the contour SP of the OAR or the like included in the treatment plan volume data VP is compared with the DV histogram HQ of the contour SQ of the OAR or the like included in the pretreatment volume data VQ, and if a difference therebetween is significant, the fact that a setting of the patient O is required again to carry out treatment based on a treatment plan can be reported to the operator. Thus, according to the radiotherapy system 1, proper treatment based on a treatment plan can be assisted.

Also, according to the radiotherapy system 1 of the first embodiment, proper treatment can be assisted by setting a treatment plan again.

Second Embodiment

An external view of a radiotherapy system 1A of a second embodiment is similar to the external view of the radiotherapy system 1 of the first embodiment shown in FIG. 1 and an entire configuration of the radiotherapy system 1A of the second embodiment is similar to the entire configuration of the radiotherapy system 1 of the first embodiment shown in FIG. 2, so that descriptions thereof are omitted.

Figure 17:
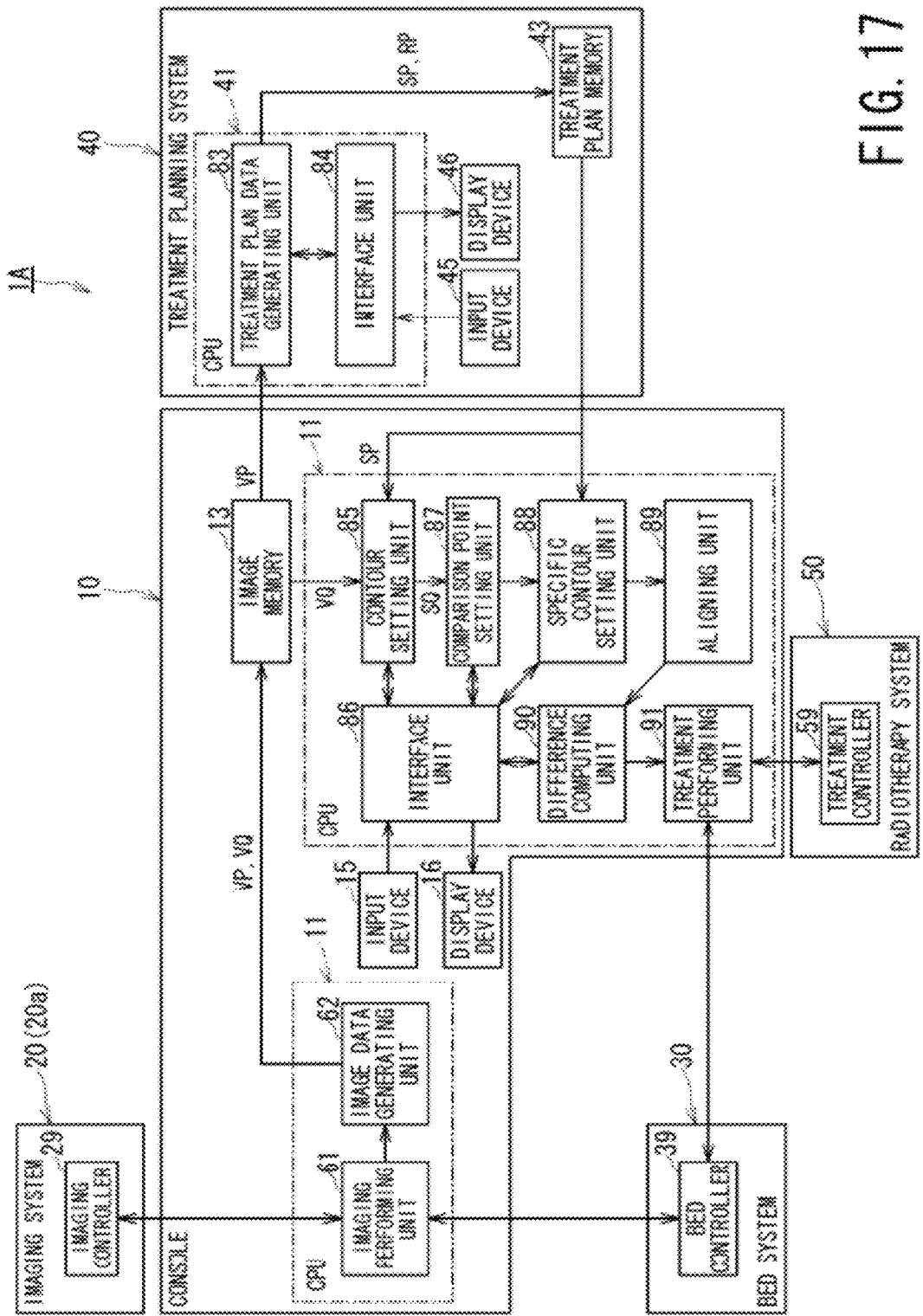
FIG. 17 is a block diagram showing functions of the radiotherapy system of a second embodiment.

FIG. 17 is a block diagram showing functions of the radiotherapy system 1A of the second embodiment.

The CPU 11 of the console 10 and the CPU 41 of the treatment planning system 40 execute programs, and thereby as shown in FIG. 17, the radiotherapy system 1A functions as the imaging performing unit 61, the image data generating unit 62, a treatment plan data generating unit 83, an interface unit 84, a contour setting unit 85, an interface unit 86, a comparison point (reference point) setting unit 87, a specific contour setting unit 88, a aligning unit 89, a difference computing unit 90, and a treatment performing unit 91. All or a part of the components 61, 62 and 83 to 91 of the radiotherapy system 1A may be included in the radiotherapy system 1A as hardware.

In the radiotherapy system 1A shown in FIG. 17, the same reference numerals are used for denoting the same functions as those in the radiotherapy system 1 shown in FIG. 3 and descriptions thereof are omitted.

The treatment plan data generating unit 83 of the treatment planning system 40 has a function of generating treatment plan data based on the treatment plan volume data VP stored in the image memory 13. When generating the treatment plan data, the treatment plan data generating unit 83 sets, on the basis of the treatment plan volume data VP, a contour SP for a structure region corresponding to structure in the patient O and sets a comparison point (isocenter) RP. The structure in the patient O includes a PTV as a treatment site, an OAR not to be irradiated, other internal organs, bones, and the like. For example, the treatment plan data generating unit 83 sets the contour SP and the comparison point RP through the interface unit 84. The contour SP and the comparison point RP set by the treatment plan data generating unit 83 are three-dimensional position information. When setting the contour SP, the treatment plan data generating unit 83 may set only one contour SP1 or may set a plurality of contours SP1, SP2 . . . .

It should be noted that it is assumed that the treatment plan data generating unit 83 generates the treatment plan data based on the treatment plan volume data VP generated by the X-ray CT system 20*a* included in the radiotherapy system 1A, but the treatment plan data generating unit 83 is not limited thereto. The treatment plan data generating unit 83 may generate the treatment plan data based on treatment plan volume data generated by an imaging system external to the radiotherapy system 1A. The treatment plan data generated by the treatment plan data generating unit 83 is stored in a storage device such as the treatment plan memory 43.

The interface unit 84 of the treatment planning system 40 is an interface such as a GUI that displays a display image that is based on the treatment plan volume data VP on the display device 46 and enables, on the display image, the operator to select the contour SP and the comparison point RP through the input device 45 operated by the operator.

The contour setting unit 85 of the console 10 has a function of setting, on the basis of the pretreatment volume data VQ stored in the image memory 13, a contour SQ corresponding to the contour SP stored in the treatment plan memory 43. For example, the contour setting unit 85 sets the contour SQ through the interface unit 86. When setting the contour SQ, the contour setting unit 85 sets only one contour SQ (SQ1) if only one contour SP (SP1) is set, and sets a plurality of contours SQ (SQ1, SQ2, . . . ) if a plurality of contours SP (SP1, SP2, . . . ) are set.

The interface unit 86 of the console 10 is an interface such as a GUI that displays on the display device 16 a display image that is based on the pretreatment volume data VQ stored in the image memory 13 and enables, on the display image, the operator to select the contour SQ through the input device 15 operated by the operator.

The comparison point setting unit 87 of the console 10 has a function of setting a comparison point RQ based on the pretreatment volume data VQ stored in the image memory 13. For example, the comparison point setting unit 87 sets the comparison point RQ through the interface unit 86. The interface unit 86 is an interface such as a GUI that displays on the display device 16 a display image that is based on the pretreatment volume data VQ stored in the image memory 13 and enables, on the display image, the operator to select the comparison point RQ through the input device 15 operated by the operator.

The specific contour setting unit 88 of the console 10 has a function of setting a specific contour s to be aligned, on the basis of the contour SP (one contour SP1, or a plurality of contours SP1, SP2, . . . ) stored in the treatment plan memory 43 and the contour SQ (one contour SQ1, or a plurality of contours SQ1, SQ2, . . . ) set by the contour setting unit 85. Examples of the specific contour s include contours of a PTV and an OAR. If the plurality of contours SP and the plurality of contours SQ corresponding thereto are set, the specific contour setting unit 88 may set one or more corresponding specific contours s of the contours SP and the contours SQ.

For example, the specific contour setting unit 88 sets a specific contour s through the interface unit 86. The interface unit 86 is an interface such as a GUI that displays on the display device 16 display images that are based on the volume data VP and the volume data VQ including the contours SP and SQ and enables, on the display images, the operator to select the specific contour s through the input device 15 operated by the operator. Also, for example, the console 10 registers identifiers of a PTV and the like in advance, and thereby the specific contour setting unit 88 may also set specific contours s corresponding to the registered identifiers.

In addition, when setting a specific contour s, the specific contour setting unit 88 may set only one specific contour s (s1) or may set a plurality of specific contours sn (s1, s2, . . . ). When setting the specific contours sn, it is desirable that the specific contour setting unit 88 should prioritize the specific contours sn for aligning.

Figure 18:
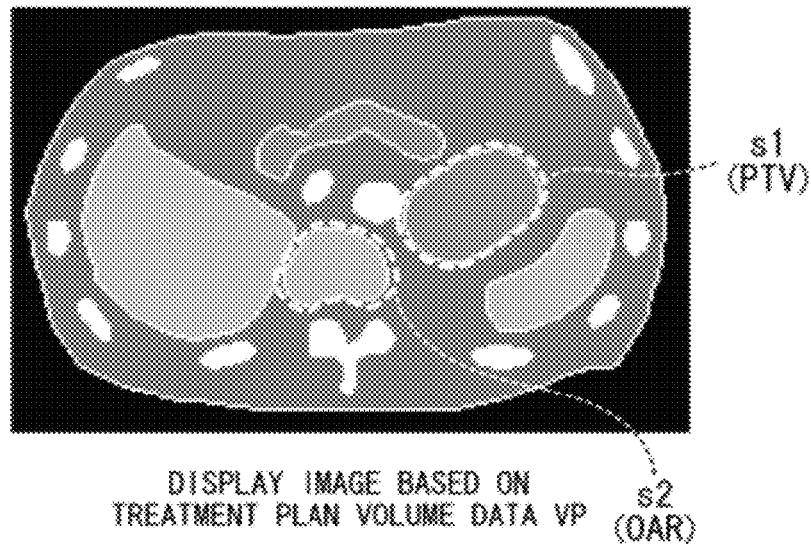
FIG. 18 a diagram schematically showing an example of a display image based on the treatment plan volume data.
Figure 19:
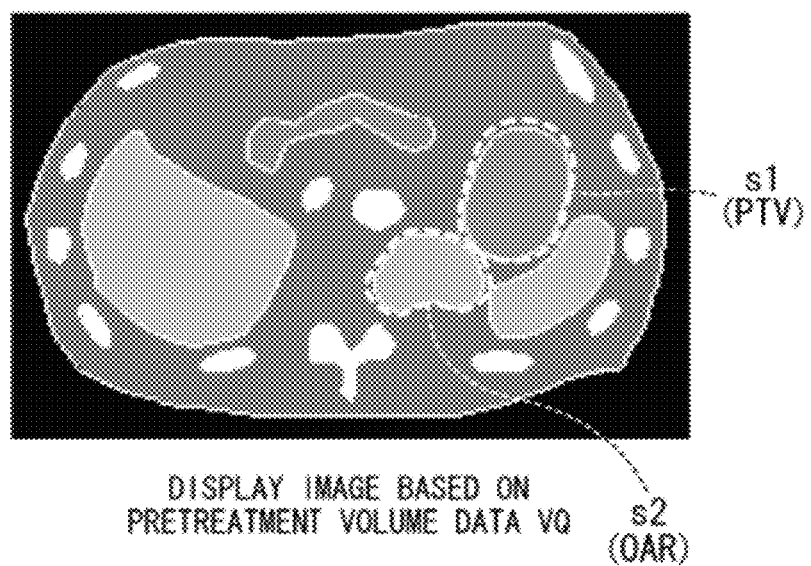
FIG. 19 is a diagram schematically showing an example of a display image based on the pretreatment volume data.

FIG. 18 a diagram schematically showing an example of a display image based on the treatment plan volume data VP. FIG. 19 is a diagram schematically showing an example of a display image based on the pretreatment volume data VQ.

FIG. 18 shows a PTV as a specific contour s1 and an OAR as a specific contour s2 of a plurality of contours SP included in a display image based on the treatment plan volume data VP. FIG. 19 is a diagram showing a PTV as a specific contour s1 and an OAR as a specific contour s2 of a plurality of contours SQ included in a display image based on the pretreatment volume data VQ. If the display image shown in FIG. 18 is compared with the display image shown in FIG. 19, it can be seen that there is a difference between the volume data VP and the volume data VQ. In FIG. 18 and FIG. 19, the specific contour setting unit 88 sets two specific contours s1 and s2 based on the contour SP of the treatment plan volume data VP and the contour SQ of the pretreatment volume data VQ.

The aligning unit 89 of the console 10 shown in FIG. 17 has a function of relatively aligning the entire volume data VP with the entire volume data VQ on the basis of the specific contour s included in the treatment plan volume data VP set by the specific contour setting unit 88 and the specific contour included in the pretreatment volume data VQ. An aligning method of the aligning unit 89 may be a method for aligning the entire volume data VP with the entire volume data VQ so as to decrease a difference in CT values (image density, values of luminance, and the like) between the specific contours s, or may be a method for aligning the entire volume data VP with the entire volume data VQ using "non-rigid bodies" linked with modification and shift of the specific contours s.

Figure 20:
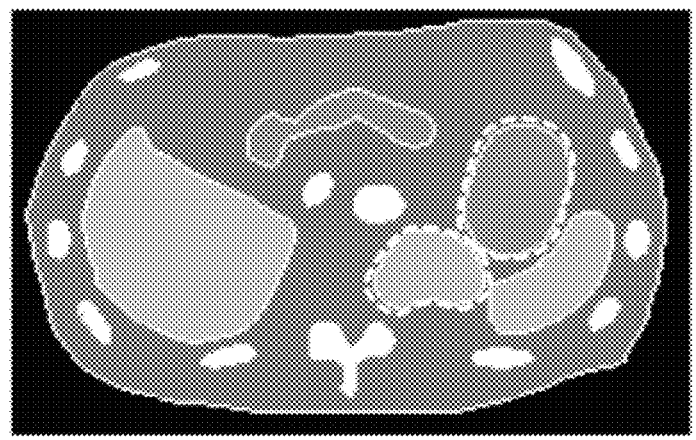
FIG. 20 is a diagram schematically showing an example of a display image based on an aligned pretreatment volume data.

In addition, in the case shown in FIG. 18 and FIG. 19, if the priority of the PTV as the specific contour s1 is higher than that of the OAR as the specific contour s2, the specific aligning unit 89 relatively aligns the entire volume data VP with the entire volume data VQ on the basis of the PTV of the treatment plan volume data VP and the PTV of the pretreatment volume data VQ. FIG. 20 is a diagram schematically showing an example of a display image based on an aligned pretreatment volume data VQ.

The difference computing unit 90 of the console 10 has a function of computing a difference (at least one of a deviation and a deviation direction in a three-dimensional coordinate system) d of the comparison point RQ included in the pretreatment volume data VQ aligned by the aligning unit 89 from the comparison point RP included in the aligned treatment plan volume data VP. The difference d computed by the difference computing unit 90 is displayed on the display device 16 through the interface unit 86.

Figure 21:
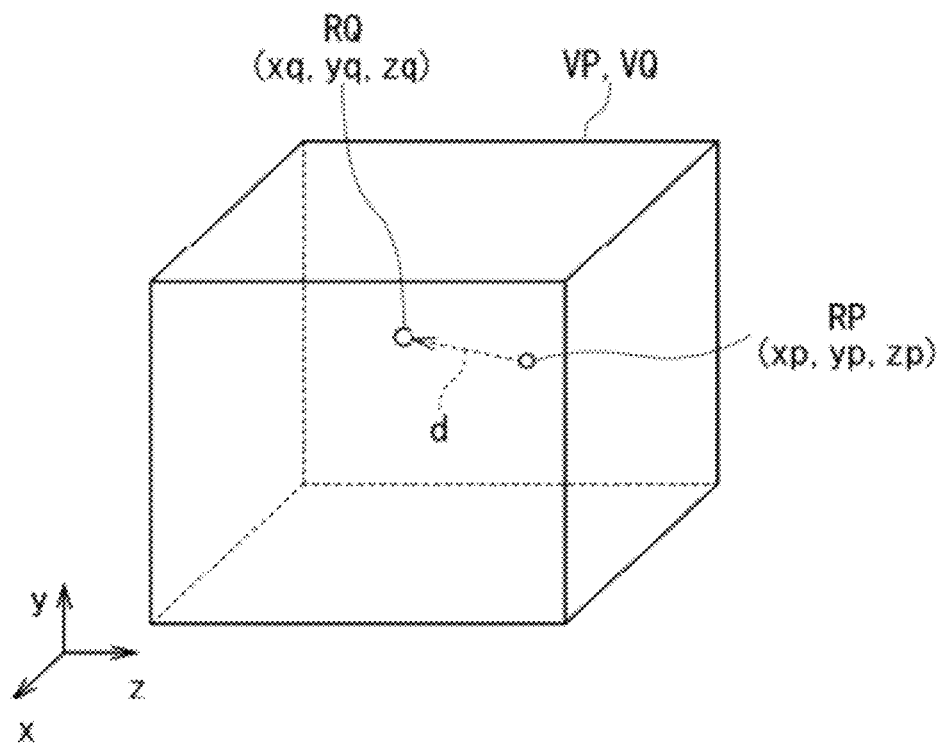
FIG. 21 is a diagram schematically showing a first display example of a difference of a comparison point.
Figure 22:
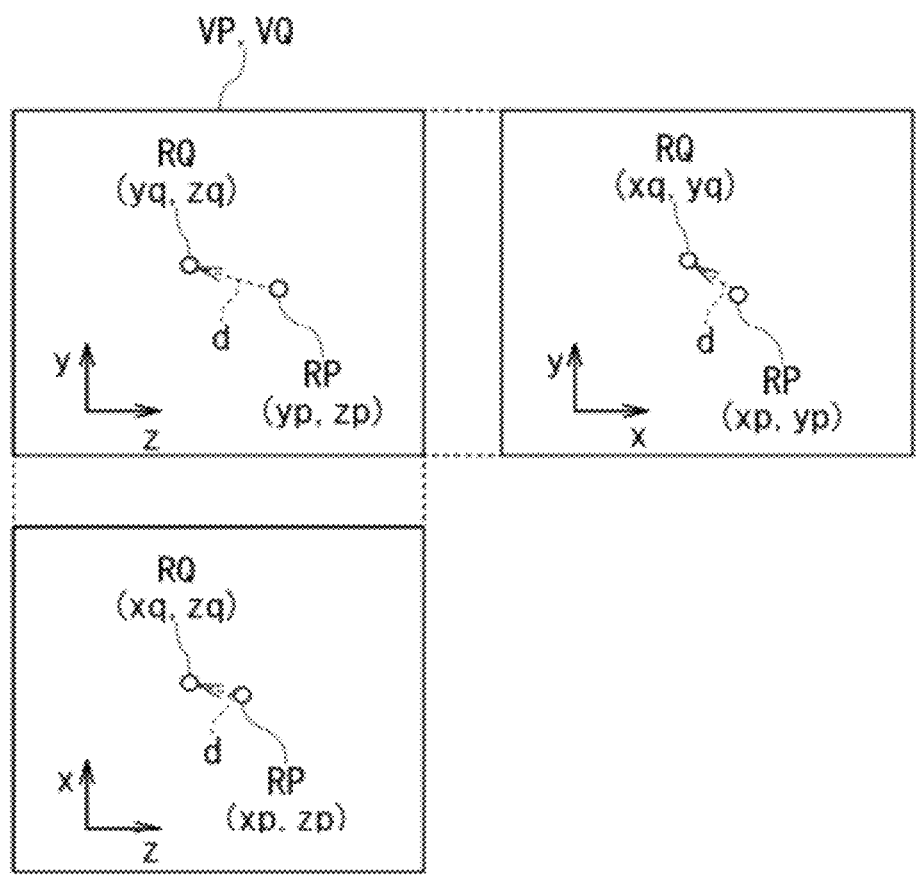
FIG. 22 is a diagram schematically showing a second display example of the difference of the comparison point.

FIG. 21 is a diagram schematically showing a first display example of a difference d of a comparison point RQ. FIG. 22 is a diagram schematically showing a second display example of the difference d of the comparison point RQ.

FIG. 21 shows a case in which both a deviation and a deviation direction as a difference d of the comparison point RQ are displayed in a three-dimensional coordinate system. FIG. 22 shows a case in which both the deviation and the deviation direction as the difference d of the comparison point RQ are displayed in a two-dimensional coordinate system. Displaying the comparison points RP and RQ as shown in FIG. 21 and FIG. 22 enables the operator to visually identify the difference d of the comparison point RQ.

The treatment performing unit 91 of the console 10 shown in FIG. 17 has a function of controlling the operations of the treatment controller 59 of the radiotherapy system 50 and the bed controller 39 of the bed system 30 to treat the treatment site of the patient O after the treatment planning system 40 reconsiders the treatment plan based on the display of the difference d of the comparison point RQ or after a setting is performed again by shifting the patient O on the table-top 33 by the difference d.

Next, an operation of the radiotherapy system 1A of the second embodiment will be described using flow charts shown in FIG. 23 and FIG. 24. In the operation of the radiotherapy system 1A shown in FIG. 23 and FIG. 24, the same reference numerals are used for denoting the same steps as those in the operation of the radiotherapy system 1 shown in FIG. 13 and FIG. 14 and descriptions thereof are omitted.

The radiotherapy system 1A sets a contour SQ corresponding to the contour SP stored in the treatment plan memory 43 based on the pretreatment volume data VQ stored in the image memory 13 in step ST13 (step ST14). The radiotherapy system 1A also sets a comparison point RQ based on the pretreatment volume data VQ stored in the image memory 13 in step ST13 (step ST35).

Figure 23:
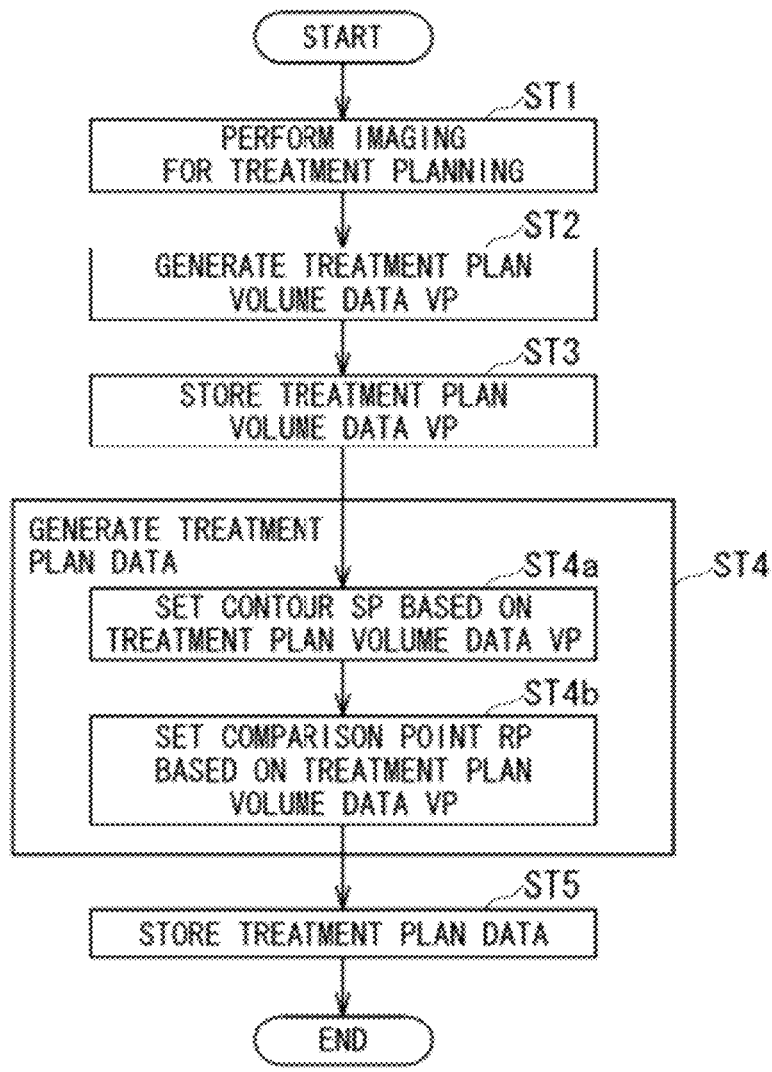
FIG. 23 is a flowchart showing the radiotherapy system of the second embodiment.
Figure 24:
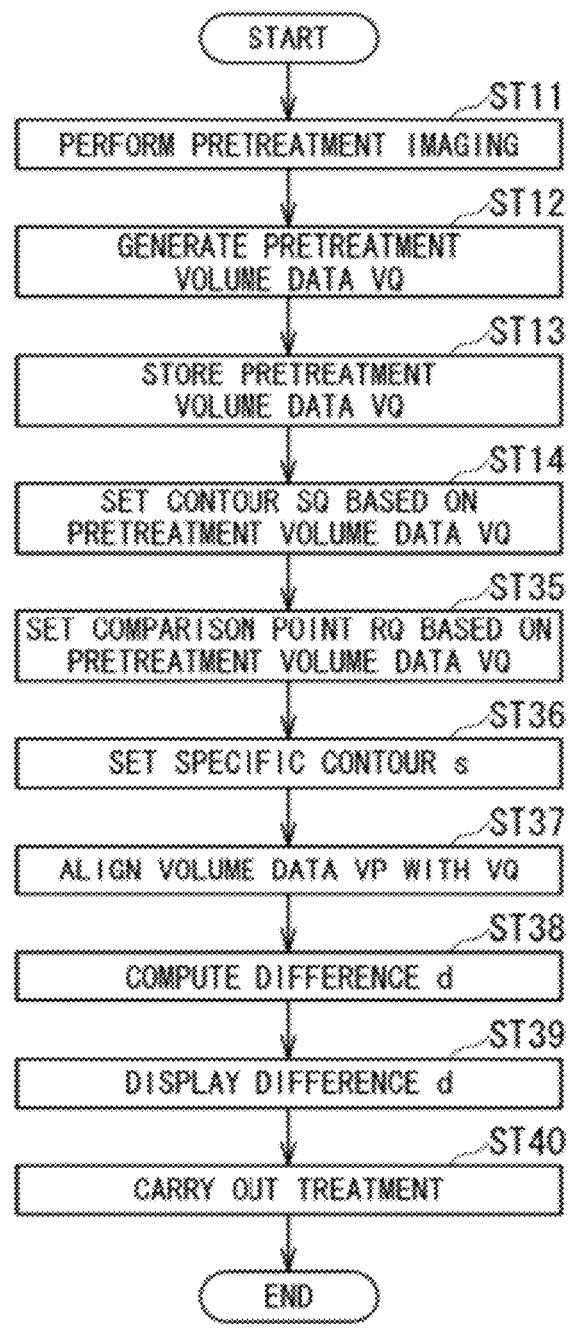
FIG. 24 is a flowchart showing the radiotherapy system of the second embodiment.

Then, the radiotherapy system 1A sets a specific contour to be aligned on the basis of the contour SP set in step ST4a of FIG. 23 and the contour SQ set in step ST14 (step ST36). Examples of the specific contour s include contours of a PTV and an OAR.

Then, the radiotherapy system 1A relatively aligns the entire volume data VP with the entire volume data VQ on the basis of the specific contour s included in the treatment plan volume data VP and the specific contour s included in the pretreatment volume data VQ, both set in step ST36 (step ST37).

Then, the radiotherapy system 1A computes a difference d of the comparison point RQ included in the pretreatment volume data VQ aligned in step ST37 from the comparison point RP included in the treatment plan volume data VP (step ST38). As shown in FIG. 21 and FIG. 22, the difference d computed in step ST38 is displayed through the display device 16 (step ST39).

Then, after the treatment planning system 40 reconsiders the treatment plan based on the difference d display in step ST39 or after a setting is performed again by shifting the patient O on the table-top 33 by the difference d, the radiotherapy system 1A controls the operations of the treatment controller 59 of the radiotherapy system 50 to treat the treatment site of the patient O (step ST40).

After the treatment site of the patient O is treated in step ST40, the radiotherapy system 1A controls the operations of the bed controller 39 of the bed system 30 to retreat the table-top 33 from the radiotherapy system 50. Then, the patient O is removed from the table-top 33 of the bed system 30 of the radiotherapy system 1A.

According to the radiotherapy system 1A of the second embodiment, since the entire treatment plan volume data VP is aligned with the entire pretreatment volume data VQ on the basis of the specific contour s included in both the volume data VP and the volume data VQ, both the volume data VP and the volume data VQ can accurately be aligned with each other. Thus, proper treatment based on a treatment plan can be assisted.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A radiotherapy system, comprising:
a placing unit;
a scanning unit;
a processing circuitry; and
a memory, wherein
the processing circuitry is configured to:
control the placing unit and the scanning unit, and perform a scan of a subject on the placing unit;
set a required region of first image data obtained by the scan, and set a corresponding required region of second image data obtained by performing a pre-scan of the subject, the required region of the first image data including a treatment organ and an organ that is not irradiated;
generate a dose-volume histogram of the required region of the first image data and generate a dose-volume histogram of the required region of the second image data;
compute a difference between the dose-volume histogram of the required region of the first image data and the dose-volume histogram of the required region of the second image data; and
output, when it is determined that the difference is greater than a threshold value, the determination,
wherein the second image data is data used in radiotherapy planning, and the first image data is data obtained after the radiotherapy planning.

2. The radiotherapy system according to claim 1, wherein the processing circuitry is configured to output, when it is determined that a maximum difference of a difference in each volume is greater than the threshold value, the determination.

3. The radiotherapy system according to claim 1, wherein the processing circuitry is configured to display the dose-volume histogram of the required region of the first image data and the dose-volume histogram of the required region of the second image data on a display.

4. The radiotherapy system according to claim 1, wherein the processing circuitry is configured to align the first image data with the second image data to set a corresponding required region in the first image data and the second image data.

5. The radiotherapy system according to claim 1, wherein the processing circuitry is configured to align the entire first image data with the entire second image data so as to decrease a difference in CT values between the first image data and the second image data, when the scanning unit is an X-ray CT system.

6. The radiotherapy system according to claim 1, wherein the image data is three-dimensional image data.

7. The radiotherapy system according to claim 1, wherein the processing circuitry is configured to generate, when it is determined that the difference is greater than the threshold value, again a dose-volume histogram of the required region of the first image data on the basis of an irradiation condition set again, and to compute a difference between the dose-volume histogram of the required region of the second image data and the dose-volume histogram generated again.

8. The radiotherapy system according to claim 1, wherein the processing circuitry is configured to:
generate, when it is determined that the difference is greater than the threshold value, again a dose-volume histogram of the required region of the first image data on the basis of an irradiation condition set again, the radiotherapy system further comprising
a display to display the dose-volume histogram of the required region of the second image data and immediately display the re-generated dose-volume histogram simultaneously with the re-generation.

9. A radiotherapy system, comprising:
a placing unit;
a scanning unit;
a processing circuitry; and
a memory, wherein
the processing circuitry is configured to:
control the placing unit and the scanning unit, and perform a scan of a subject on the placing unit;
store therein first image data obtained by performing a pre-scan of the subject in radiotherapy planning;
store therein position information of a required region included in the first image data, the required region including a treatment organ and an organ that is not irradiated; and
use the position information of the required region to align the first image data with second image data,
wherein the first image data is data used in radiotherapy planning, and the second image data is data obtained after the radiotherapy planning.

10. The radiotherapy system according to claim 9, wherein the processing circuitry is configured to:
store therein the position information of the required region included in the first image data and position information of the required region included in the second image data; and
align the first image data with the second image data by using the position information of the required region of the first image data and the position information of a required region of the second image data.

11. The radiotherapy system according to claim 9, wherein the processing circuitry is configured to compute at least one of a deviation and a deviation direction of the aligned second image data from the aligned first image data.

12. The radiotherapy system according to claim 11, wherein
the processing circuitry is configured to:
set a comparison point for each of the first image data and the second image data; and
compute at least one of the deviation and the deviation direction of the comparison point set in the aligned second image data from the comparison point set in the aligned first image data.

13. The radiotherapy system according to claim 9, wherein the processing circuitry is configured to align the entire first image data with the entire second image data so as to decrease a difference in CT values between the required region of the first image data and a required region of the second image data, when the scanning unit is an X-ray CT system.

14. The radiotherapy system according to claim 9, wherein the image data is three-dimensional image data.

15. The radiotherapy system according to claim 9, wherein the processing circuitry is configured to:
store, when the required region is set for a plurality of regions, therein an order of priority for aligning; and
align the first image data with the second image data in the order of priority.

16. A control method for a radiotherapy system that includes a placing unit and a scanning unit, the method comprising:
controlling the placing unit and the scanning unit, and performing a scan of a subject on the placing unit;
setting a required region of first image data obtained by the scan, and setting a corresponding required region of second image data obtained by, before the scan, performing a pre-scan of the subject, the required region of the first image data including a treatment organ and an organ that is not irradiated;
generating a dose-volume histogram of the required region of the first image data and generating a dose-volume histogram of the required region of the second image data;
computing a difference between the dose-volume histogram of the required region of the first image data and the dose-volume histogram of the required region of the second image data; and
outputting a determination when it is determined that the difference is greater than a threshold value,
wherein the second image data is data used in radiotherapy planning, and the first image data is data obtained after the radiotherapy planning.

17. The control method according to claim 16, further comprising:
setting position information of the required region included in the second image data obtained by the pre-scan in radiotherapy planning, and
aligning the second image data with the first image data obtained by the scan in radiotherapy planning, by using the position information.

18. The control method according to claim 17, further comprising:
setting a comparison point for each of the first image data and the second image data, and
computing at least one of a deviation and a deviation direction of the comparison point set in the aligned second image data from the comparison point set in the aligned first image data.

19. The radiotherapy system according to claim 1, further comprising a display, wherein
the processing circuitry is configured to report an abnormality to an operator through the display.

* * * * *